(12) United States Patent
Tessier

(10) Patent No.: US 11,648,143 B2
(45) Date of Patent: May 16, 2023

(54) MULTIFUNCTIONAL BRACE

(71) Applicant: Emmanuelle Tessier, Town of Mount-Royal (CA)

(72) Inventor: Emmanuelle Tessier, Town of Mount-Royal (CA)

( * ) Notice: Subject to any disclaimer, the term of this patent is extended or adjusted under 35 U.S.C. 154(b) by 959 days.

(21) Appl. No.: 15/419,127

(22) Filed: Jan. 30, 2017

(65) Prior Publication Data

US 2017/0216074 A1 Aug. 3, 2017

(30) Foreign Application Priority Data

Jan. 28, 2016 (CA) ...................................... 2919429

(51) Int. Cl.
*A61F 5/00* (2006.01)
*A61F 5/01* (2006.01)

(52) U.S. Cl.
CPC .................................. *A61F 5/0123* (2013.01)

(58) Field of Classification Search
CPC .... A61F 5/0106; A61F 5/0109; A61F 5/0123; A61F 2005/0176; A61F 5/30; A61F 5/0104; A61F 5/0118; A61F 13/061; A61F 13/062; A61F 13/08; A61F 13/085; A61F 2005/0181; A63B 2071/125
USPC ............................................... 602/26, 23, 24
See application file for complete search history.

(56) References Cited

U.S. PATENT DOCUMENTS

| 1,388,772 | A | | 8/1921 | Sheehan | |
|---|---|---|---|---|---|
| 2,220,836 | A | | 11/1940 | Closson | |
| 2,270,685 | A | | 1/1942 | Miller | |
| 3,046,981 | A | | 7/1962 | Biggs et al. | |
| 3,406,406 | A | * | 10/1968 | Lutz | A61F 5/0118 2/24 |
| 3,945,046 | A | | 3/1976 | Stromgren | |
| 4,084,584 | A | | 4/1978 | Detty | |
| 4,116,236 | A | * | 9/1978 | Albert | A41D 13/065 2/24 |
| 4,296,744 | A | | 10/1981 | Palumbo | |
| 4,607,628 | A | | 8/1986 | Dashefsky | |
| 4,777,946 | A | | 10/1988 | Watanabe et al. | |
| 4,870,956 | A | * | 10/1989 | Fatool | A61F 5/0109 602/26 |
| 4,964,402 | A | * | 10/1990 | Grim | A61F 5/0111 602/2 |
| 4,993,409 | A | * | 2/1991 | Grim | A61F 7/007 602/19 |
| 5,255,391 | A | * | 10/1993 | Levine | A41D 13/0568 2/24 |

(Continued)

*Primary Examiner* — Adam Baker

(57) ABSTRACT

A brace for aligning and protecting a patella. The brace includes a mounting component for mounting the brace to the leg of the user. The brace also includes a first attachment component attached to the mounting component and a second attachment component superposed on the first attachment component. An alignment component for aligning the patella is releasably attached to the mounting component by the first attachment component. A cushioning component for cushioning the patella is releasably attached to the mounting component by the second attachment component. A cryotherapy or thermal therapy component can alternatively be releasably attached to the mounting component by the second attachment component instead of the cushioning component depending on the needs of the user.

19 Claims, 2 Drawing Sheets

(56) References Cited

U.S. PATENT DOCUMENTS

| | | | |
|---|---|---|---|
| 5,711,029 A * | 1/1998 | Visco | A41D 13/0568 |
| | | | 2/22 |
| 7,004,919 B2 | 2/2006 | Gaylord et al. | |
| 7,083,586 B2 * | 8/2006 | Simmons | A61F 5/0109 |
| | | | 602/23 |
| 7,237,270 B2 * | 7/2007 | Crye | A41D 13/0575 |
| | | | 2/24 |
| 7,625,350 B2 | 12/2009 | Hunter et al. | |
| 7,749,181 B2 | 7/2010 | Simmons et al. | |
| 2014/0330184 A1 * | 11/2014 | Kilbey | A61F 5/0123 |
| | | | 602/13 |
| 2015/0335457 A1 * | 11/2015 | Bauer | A61F 13/062 |
| | | | 602/26 |

* cited by examiner

MULTIFUNCTIONAL BRACE

FIELD OF THE INVENTION

The present invention relates to the general field of orthopedic braces and is more particularly concerned with a multifunctional brace for use on a human joint for providing cushioning, guiding and therapeutic functions.

BACKGROUND

Braces are used in a variety of situations to provide assistance to impaired human joints. For example, braces can be used to assist an intended user suffering from so-called patellofemoral syndrome, one of the leading causes of knee pain.

As the name implies, the patellofemoral syndrome implicates the femur and the patella. It results from an imbalance in the forces controlling the sliding of the patella relative to the femur.

The patella acts as a lever for augmenting the extension force of the quadriceps muscle. It is attached to the quadriceps muscle by a tendon and to the tibia by a ligament. It is centered in a notch formed between the distal condyles at the extremity of the femur.

During the flexion motion of the knee, the patella slides downwards, while it slides upwards during extension of the leg at the knee. To facilitate the sliding action in the femoral notch, the contact surfaces between the patella and the femur are covered by a cartilage.

In a healthy knee, balance between the various anatomical structures maintains the patella in proper alignment in the femoral notch. Various conditions may cause misalignment of the patella, hence creating friction and wear on the cartilage. One of the most frequent causes of misalignment is an imbalance between the internal and external portions of the quadriceps muscle.

Uneven distribution of the frictional forces between the patella and the femur often results in pain during and after an activity requiring flexion of the knee, a common symptom of patellofemoral syndrome. Depending on the level of irritation, the pain may even be present when a person merely sits down for a prolonged period. Furthermore, friction can create inflammation and result in premature wear of the cartilage.

Existing solutions for sport enthusiasts suffering from patellofemoral syndrome but wanting to remain active in sports requiring knee protection like volleyball include protecting the knees by wearing conventional volleyball knee pads during games and wearing conventional patellar braces between games. In order to limit inflammation cryotherapy with an icing pad can also be used after play. Heat or thermotherapy components can also be used during off periods in an effort to promote healing.

Conventional volleyball knee pads include a cushion adapted to minimize the impact of the knees on the ground during so-called dives. The cushion is typically relatively thick and usually made of elastomeric foam. It is typically held in place on the user's knee by a tubular sleeve made of an elastic material such as Neopren© slidably mounted on a user's leg.

Knee pads must be fitted to the player's morphology. When too small, they are uncomfortable and hinder the player's focus during play. When too big, they are prone to slide down the calf, especially when the player moves suddenly.

Conventional patellar braces promote healing through a plurality of functions such as patellar centering and articular joint stabilisation. Multiple types exist depending on the stiffness required and whether or not progressive centering is provided. They are typically provided with a guiding plate having a guiding aperture extending therethrough. The guiding aperture is configured for surrounding the patella. The guiding aperture is adapted to center the patella with minimal compression thereon.

Cryotherapy components are commonly used in the acute phase of injury to prevent inflammation. They provide multiple physiological effects such as shrinking of blood vessels and reducement of inflammation and swelling. They also help to slowdown the cellular metabolism, reducing the production of toxins. Furthermore, they reduce the temperature of the epidermis, providing an analgesic effect.

Thermotherapy components are used in the rehabilitation phase to promote healing or in the pre-activity phase to warm-up the joint. Thermotherapy components are also associated with a plurality of potentially beneficial physiological effects such as dilating the blood vessels to enhance the oxygen and nutrient input towards the healing site. They also reduce stiffness and contribute to pain management.

Various types of cryotherapy and thermotherapy components are available. They are typically divided in two main sub-types namely the so-called "passive" type of components, such a gel bags, damp towels or the like and the so-called "active" type of components using a chemical reaction to generate heat or cold.

None of the existing solutions offers in a synergistic manner the combination of functions provided individually by the three existing types of components namely knee pads, knee braces and cryotherapy or thermotherapy components.

In theory, one could try to use simultaneously the three types of components by superposing or overlaying them in an attempt to combine their respective individual functions. However, this approach leads to several drawbacks.

Indeed, there exists a plurality of reasons why conventional knee pads are not adapted to be superposed on conventional patellar braces. For example, the overlay of their respective tubular attachment sections is associated with a cumbersome double layer structure leading to discomfort for the user, especially at the back of the knee.

Furthermore, the overlay of a conventional knee pad over a conventional knee brace imparts pressure on the knee brace transmitting the pressure to the patella, hence potentially aggravating the patellofemoral syndrome.

Also, even if the knee pad is snuggly fitted over the knee brace, impact on the ground may create a relative movement between the two structures. Still furthermore, mounting of the knee pad over the knee brace by an intended user is tedious and time consuming.

With regards to conventional components used for cryotherapy and thermotherapy, there are not adapted to be used in combination with conventional knee pads or braces. Indeed, the mere overlay of cryotherapy or thermotherapy components without attachment thereof does not allow the user to walk around while benefiting from the protecting or therapeutic effects of such components.

Furthermore, conventional knee braces are not adapted to be worn in the context of a practice or game of a sport such as volleyball that often requires that the player performs so-called dives with the knees impacting the ground. When used in such contexts, they have a tendency to deteriorate rapidly. Accordingly, some individuals only wear knee braces before returning to play, depriving their patella of guidance in the critical return to play period.

Still furthermore, the use of three distinct components, namely a knee brace, a knee pad and a cryotherapy pad is associated with various drawbacks such as the need to purchase three different objects. Also, the three objects take up valuable storage space in the carrying bag of the user and are at greater risk of one of the items getting lost.

Accordingly, there exists a need for a multifunctional structure better adapted to the needs of individuals that wish to continue practicing sporting activities while promoting healing and protection of their body joints.

There exists a need for a structure adapted for use during sport that simultaneously protects the knees against impact and guides the patella in its notch between the condyles of the femur.

It is a general object of the present invention to provide a multifunctional brace combining the functions associated with conventional knee pads, knee braces and optionally thermal or cryotherapy components.

The proposed multifunctional brace not only allows a single structure to offer the combined functions associated with the individual structures, but also synergistically optimizes such functions.

The proposed multifunctional brace further allows the intended user to customize such functions depending on individual variables such as the level of recovery reached by the user.

SUMMARY OF THE INVENTION

In accordance with an embodiment of the invention, there is provided a brace for aligning and protecting a patella part of a knee of a leg of an intended user, the patella being attached to a patellar tendon, the brace comprising. The brace includes a mounting component for mounting the brace to the leg of the user. The brace also includes a first attachment component attached to the mounting component and a second attachment component, the second attachment component being in a substantially superposed relationship relative to the first attachment component.

The brace further includes an alignment component for aligning the patella, the alignment component being attached to the mounting component by the first attachment component. The brace still further includes a cushioning component for cushioning the patella against impact threreon, the cushioning component being attached to the mounting component by the second attachment component.

Typically, the cushioning component is releasably attached to the mounting component by the second attachment component and the alignment component is releasably attached to the mounting component by the first attachment component.

Conveniently, the brace also includes a therapeutic component for promoting the health of the knee, the therapeutic component being releasably attachable to the mounting component by the first attachment component. The alignment component and the therapeutic component are typically adapted to be alternatively attached to the mounting component by the first attachment component.

Typically, the therapeutic component is a thermal component for changing the temperature of the knee of the intended user.

Conveniently, the mounting component is a substantially tubular sleeve configured and sized to be worn on the leg of the intended user, and the first attachment component is a first attachment pocket extending from the sleeve for receiving the alignment component, the first attachment pocket being positioned so as to be positioned substantially over the knee when the sleeve is worn by the user.

Typically the second attachment component is a second attachment component pocket, the second attachment pocket being in a substantially overlapping relationship relative to the first attachment pocket.

Conveniently, the tubular sleeve is provided with a sleeve window extending therethrough, the sleeve window being substantially in register at least a portion of the first attachment pocket for allowing the at least a portion of the first attachment pocket to be in contact with the knee of the intended user and at least a portion of the alignment component to be in a more proximal relationship with the knee of the intended user then it would be without the sleeve window.

Typically, the alignment component includes an alignment pad, the alignment pad being provided with an alignment aperture, the alignment aperture defining an alignment aperture inner edge, the alignment aperture inner edge being configured an sized for substantially surrounding at least a portion of the patella of the intended user.

Conveniently, the alignment aperture inner edge has a substantially circular main edge segment and an auxiliary edge segment, the auxiliary edge segment being configured and sized for surrounding at least a portion of the patellar tendon.

Typically, the alignment pad defines an alignment pad inner surface and an alignment pad outer surface, the alignment pad being provided with an abutment component extending from the alignment pad inner surface Conveniently, the cushioning component is a cushioning pad, the cushioning pad being made of an impact absorbing material.

In one embodiment of the invention, the therapeutic component is an icing pad for icing the knee of the user, the icing pad being provided with an icing pad aperture extending therethrough, the icing pad aperture defining an icing pad aperture peripheral edge, the icing pad aperture peripheral edge being configured and sized for substantially surrounding the patella; wherein the icing pad aperture allows the icing pad to cool around the patella without directly icing the patella.

In an alternative embodiment of the invention, the brace also includes a medializing component for progressively medializing the position of the patella of the intended user.

In yet another alternative embodiment of the invention, there is provided a brace for protecting a patella part of a knee of a leg of an intended user with a cushioning component and aligning the patella with an alignment component. The brace includes a mounting component for mounting the brace to the leg of the user. The brace also includes a first attachment component attached to the mounting component for attaching the cushioning component to the mounting component so that at least a portion of the cushioning component is positioned substantially over the knee when the mounting component is mounted on the leg of the intended user. The brace further includes a second attachment component for attaching the alignment component to the mounting component, the second attachment component being in a substantially superposed relationship relative to the first attachment component so that the alignment component is positioned between the knee and the cushioning component when the mounting component is mounted on the leg of the intended user.

BRIEF DESCRIPTION OF THE DRAWINGS

Embodiments of the present invention will now be described, by way of example, in reference to the following drawings in which.

DETAILED DESCRIPTION

Figure 1:
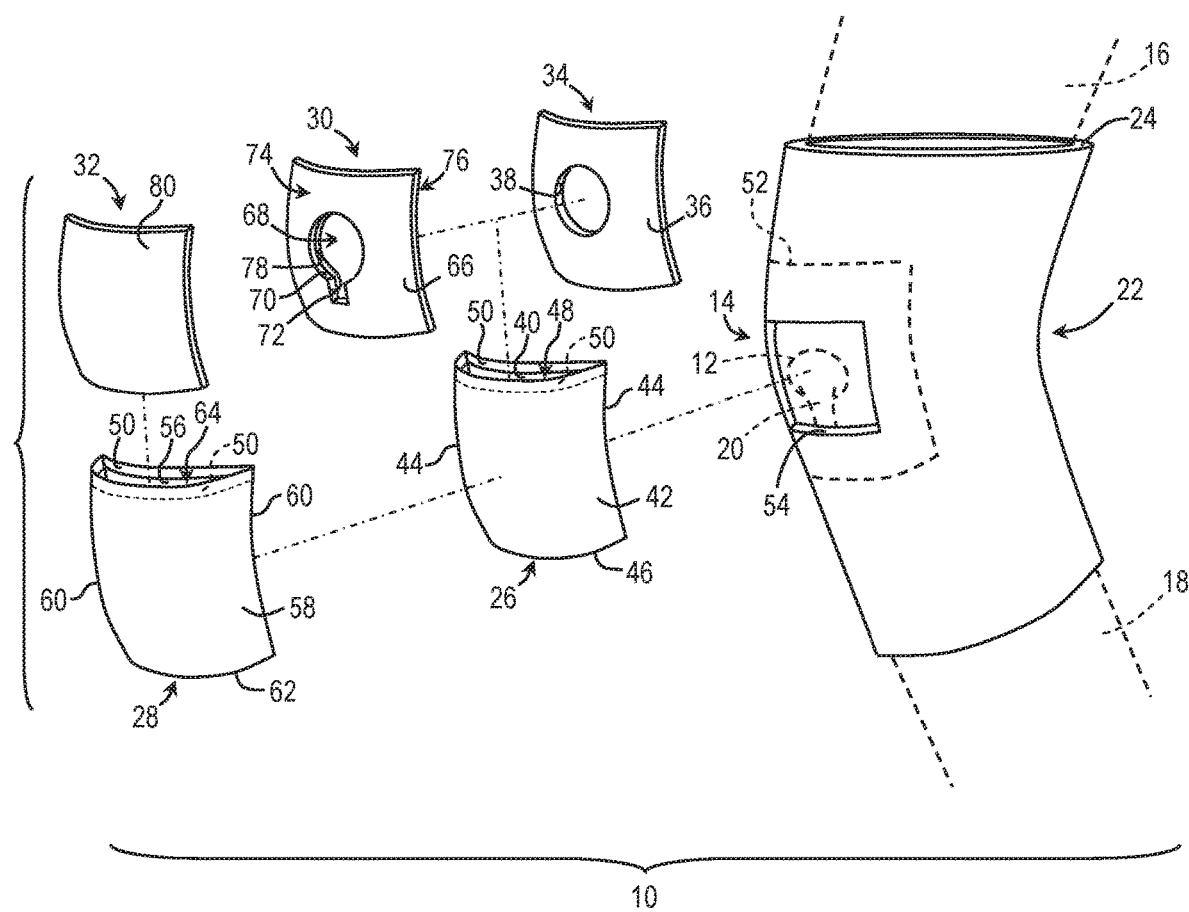
FIG. 1: In an exploded view, illustrates some of the components of a brace in accordance with an embodiment of the present invention, the brace being shown mounted on a segment of a leg of an intended user.
Figure 2:
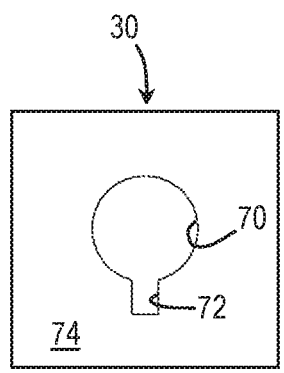
FIG. 2: In a front elevational view illustrates an alignment component part of a knee brace in accordance with an embodiment of the present invention.

With reference to FIG. 1, there is shown a multifunctional brace 10 in accordance with an embodiment of the present invention, generally indicated by the reference numeral 10. The brace 10 is intended to be used for aligning and protecting a patella 12 (schematically illustrated in phantom lines) part of a knee 14 of a leg of an intended user. The knee 14 allows bending of the leg between an upper leg segment 16 and a lower leg segment 18. As is well known, the patella 12 is attached to a patellar tendon 20 (also shown in phantom lines).

Although the brace 10 is described as a knee brace, it should be understood that the brace 10 could be used with slight modifications on different body parts such as elbows, ankles, wrists or any other suitable body part without departing from the scope of the present invention.

The brace 10 includes a mounting component 22 for mounting the brace 10 to the leg of the user. The mounting component 22 typically takes the form of a tubular sleeve 24 made of a substantially elastomeric material. For example, the mounting component could be made of Neoprene© or any other suitable material. In such instances, the sleeve 24 is configured and sized so as to be slidable over the knee 14 and to be frictionally retained in proper alignment with the knee 14 without causing discomfort to the user.

Also, the mounting component 22 could include two or more mounting component segments (not shown) attached to the upper leg segment 16 and lower leg segment 18. In such instances, the mounting component segments could be made of more rigid material and attached together by a hinge.

The brace 10 also includes a first attachment component 26 attached to the mounting component 22. The brace 10 further includes a second attachment component 28. The second attachment component 28 is typically in a substantially superposed relationship relative to the first attachment component 26.

Typically, the brace 10 also has an alignment component 30 for aligning the patella 12 in a proper position within the femoral notch formed by the condyles at the distal end of the femur. The alignment component 30 is attached to the mounting component 22 by the first attachment component 26.

Typically, the brace 10 further includes a cushioning component 32 for cushioning the patella against impact threreon. The cushioning component 32 is attached to the mounting component 22 by the second attachment component 28.

Preferably, the cushioning component 32 is releasably attached to the mounting component 22 by the second attachment component 28. Also preferably, the alignment component 30 is releasably attached to the mounting component 22 by the first attachment component 26.

Typically, the brace 10 further includes a therapeutic component 34 for promoting the health of the knee 14. The therapeutic component 34 is releasably attachable to the mounting component 22 by the first attachment component 26. In use, the alignment component 30 and the therapeutic component 34 are adapted to be alternatively attached to the mounting component 22 by the first attachment component 26.

In one embodiment of the invention, the therapeutic component 34 takes the form of a therapeutic pad 36. The therapeutic pad 36 can be a cryotherapy pad used for icing anatomical structures around the patella such as tendons and ligaments. In such instance the therapeutic pad 36 is provided with an icing pad aperture 38 extending therethrough.

The icing pad aperture 38 defines an icing pad aperture peripheral edge configured and sized for substantially surrounding the patella 12. The icing pad aperture 38 hence allows the icing pad 36 to cool around the patella 12 without directly icing over the patella 12.

The therapeutic pad 36 could also be used as a thermal therapy pad for delivering heat to the anatomical structures around the patella 12. The therapeutic pad 36 could further be used for delivering analgesic or therapeutic substances or for any other suitable therapeutic action without departing from the scope of the present invention.

In one embodiment of the invention, the first attachment component 26 includes a first attachment pocket extending from the sleeve 24 for receiving the alignment component 30 or the therapeutic component 34. The first attachment pocket is positioned so as to be positioned substantially over the knee 14 when the sleeve 24 is worn by the user.

The first attachment pocket typically includes a first pocket inner wall 40 and a first pocket outer wall 42. The first pocket inner wall 40 and first pocket outer wall 42 are attached together along their respective side and bottom edges so as to define a pair of closed first pocket side edges 44 and a closed first pocket bottom edge 46. The first attachment pocket defines a first pocket mouth 48 for slidably receiving the alignment component 30 or the therapeutic component 34.

The first pocket mouth 48 can be closed by joining the top edges of the first pocket inner wall 40 and the first pocket outer wall 42. for selectively preventing withdrawal of components inserted in the first attachment pocket. The first pocket mouth 48 is typically provided with a first mouth releasable locking means for releasably locking the first pocket mouth in a closed position.

In one embodiment of the invention, the first mouth releasable locking means includes cooperating strips 50 of Velcro© extending along the inner surface of the first pocket inner wall 40 and the first pocket outer wall 42 adjacent their respective top edges. The first mouth releasable locking means can take the form of a zipper-type mechanism, a locking flap or any other suitable means without departing from the scope of the present invention.

When the first attachment component 26 takes the form of a first attachment pocket, the peripheral edges of the first pocket inner wall 40 are attached to the mounting component 22 using a pocket-to-mounting component attachment means designated by the reference numeral 52. The pocket-to-mounting component attachment means 52 may take the form of stitches, thermal welding lines or any other suitable means without departing from the scope of the present invention.

The tubular sleeve 24 is typically provided with a sleeve window 54 extending therethrough. The sleeve window 54 is typically substantially in register with at least a portion of the first pocket inner wall 40 for allowing the at least a portion of the first pocket inner wall 40 to be in contact with the knee 14 of the intended user. The sleeve window 54 also allows at least a portion of the alignment component 30 to be in a more proximal relationship with the knee 14 of the intended user then it would be without the sleeve window 54.

In one embodiment of the invention, the second attachment component 28 includes a second attachment pocket for receiving the cushioning component 32. The second attachment pocket is positioned so as to be in a substantially overlapping relationship relative to the first attachment pocket.

The second attachment pocket typically includes a second pocket inner wall 56 and a second pocket outer wall 58. The second pocket inner wall 56 and second pocket outer wall 58 are attached together along their respective side and bottom edges so as to define a pair of closed second pocket side edges 60 and a closed second pocket bottom edge 62. The second attachment pocket defines a second pocket mouth 64 for slidably receiving the cushioning component 32.

The second pocket mouth 64 can be closed by approaching the top edge of the second pocket inner wall 56 and the second pocket outer wall 58 for selectively preventing withdrawal of components inserted in the second attachment pocket. The second pocket mouth 64 is typically provided with a second mouth releasable locking means for releasably locking the second pocket mouth in a closed position.

In one embodiment of the invention, the second mouth releasable locking means includes cooperating strips 50 of Velcro© extending along the inner surface of the second pocket inner wall 56 and the second pocket outer wall 58 adjacent their respective top edges. The second mouth releasable locking means can take the form of a zipper-type mechanism, a locking flap or any other suitable means without departing from the scope of the present invention.

When the second attachment component 28 takes the form of a second attachment pocket, the peripheral edges of the second pocket inner wall 56 are attached to the mounting component 22 using a pocket-to-mounting component attachment means designated by the reference numeral 52. The pocket-to-mounting component attachment means 52 may take the form of stitches, thermal welding lines or any other suitable means without departing from the scope of the present invention.

The alignment component 30 typically includes an alignment pad 66. The alignment pad 66 is typically provided with an alignment aperture 68. The alignment aperture 68 defines an alignment aperture inner edge. The alignment aperture inner edge is configured and sized for substantially surrounding at least a portion of the patella 12 of the intended user.

In a preferred embodiment of the invention, the alignment aperture inner edge has a substantially circular main edge segment 70 and an auxiliary edge segment 72. The auxiliary edge segment 72 is configured, sized and positioned for surrounding at least a portion of the patellar tendon 20 when the sleeve 24 is properly positioned over the knee 14.

Figure 3:
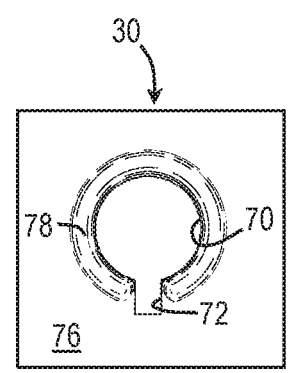
FIG. 3: In a rear elevational view illustrates an alignment component part of a knee brace in accordance with an embodiment of the present invention.

Typically, the alignment pad 66 defines an alignment pad inner surface 74 and an alignment pad outer surface 76. As shown more specifically in FIG. 3, the alignment pad 66 is provided with an abutment component 78 extending from the alignment pad inner surface 76 adjacent the main edge segment 70.

The abutment component 78 is shown having the configuration of an interrupted and truncated torus, the torus being circumferentially truncated in half and interrupted about the auxiliary edge segment 72. It should however be understood that the abutment component 78 could have any other suitable shape without departing from the scope of the present invention.

In a preferred embodiment of the invention, the cushioning component 32 is a cushioning pad 80. The cushioning pad 80 is made of an impact absorbing material.

The first and second pockets, the therapeutic pad 36, the alignment pad 66 and the abutment component 78 are all shown throughout the drawings has having a substantially parallelepiped-shaped configuration. It should however be understood that these component could have any other suitable configuration without departing from the scope of the present invention.

Figure 4:
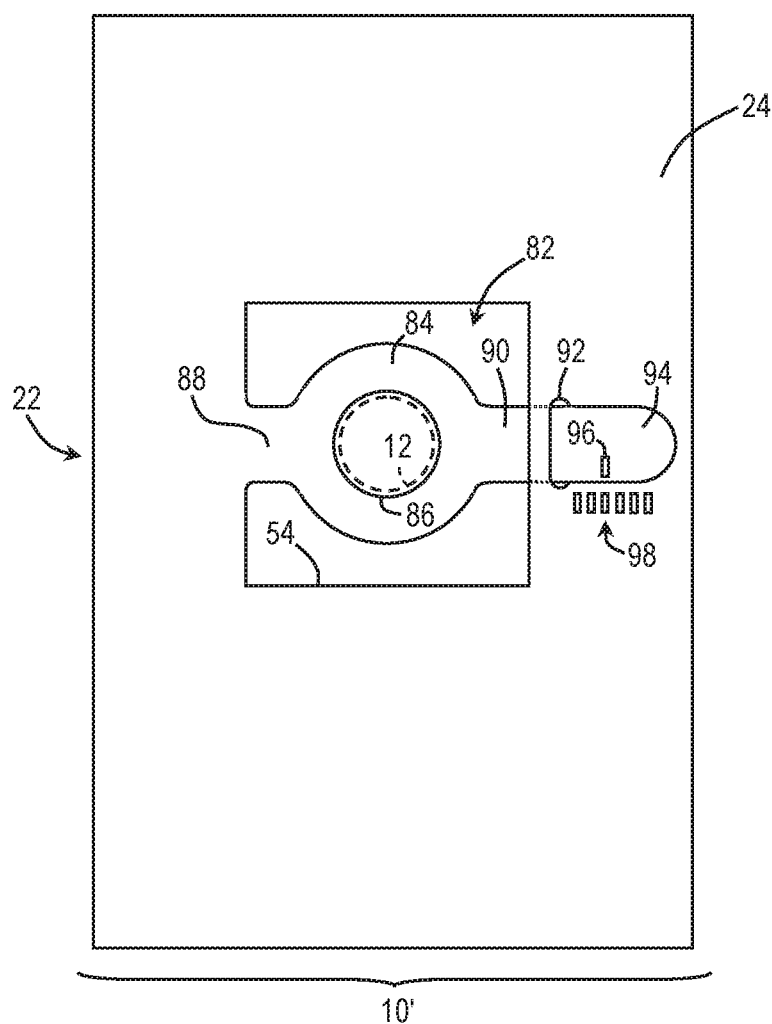
FIG. 4: In a front elevational view illustrates a sleeve having a progressive medializing component, the sleeve being part of a knee brace in accordance with an alternative embodiment of the present invention.

In an alternative embodiment of the invention, illustrated more specifically in FIG. 4, there is shown a brace 10' further including a medializing component 82 for progressively medializing the position of the patella 12 of the intended user.

Since the brace 10' is otherwise similar to the previously described brace 10, similar reference numeral will be used to designate similar components and only the sleeve 24 and associated medializing component 82 will be shown. It should however be understood that the brace 10' includes the other components of brace 10.

The medializing component 82 includes a medializing tongue 84 extending from the mounting component 22. The medializing tongue 84 has a medializing aperture extending therethrough. The medializing aperture defines a medializing edge 86 for abutting against a lateral portion of the patella 12.

The medializing component 82 is provided with an adjustment means for allowing the intended user to adjust the position of the medializing edge relative to the mounting component 22. The adjustment means preferably acts also acts as a biasing means for biasing the patella towards proper alignment.

In the embodiment illustrated in FIG. 4, the medializing component 82 includes a medializing component attachment section 88 for attachment to the mounting component 22. At least a portion of the medializing component attachment section 88 is made of reversibly deformable or elastic material.

The medializing component 82 also includes a medializing component locking segment 90 extending from the medializing tongue substantially opposite the medializing component attachment section 88 for releasably locking the medializing edge 86 in a predetermined relationship relative to the mounting component 22

A terminal portion 94 of the medializing component locking segment 90 extends underneath the inner surface of the sleeve 24 through a tongue aperture 92 formed in the sleeve 24. A tongue fixing means (not shown) such as a pair of Velcro© strips, a clip or any other suitable means is used for releasably locking the terminal portion 94 to the exterior surface of the sleeve 24.

A marking system may be used for providing a visual clue to the intended user about the progression of the medialization an allowing for more precise adjustment of the position of the of the medializing edge 86.

In the illustrated embodiment, the marking system includes a tongue line 96 marked on the terminal portion 94 and lines 98 on an adjacent section of sleeve 24. It should however be understood that any other suitable marking means could be used without departing from the scope of the present invention.

In use, the user pulls on the medializing component locking segment 90 stretching the elastic portion of the medializing component attachment section 88 and allowing lateral displacement of the medializing edge 86. The elastic portion of the medializing component attachment section 88 is prevented for springing back to its original configuration by the tongue fixing means.

At given intervals of time, when judged appropriate, the tongue fixing means is temporarily released so as to allow the elastic portion of the medializing component attachment section 88 to gradually spring back, by increments, towards its original configuration, hence allowing the medializing edge 86 to gradually medialize the patella 12.

In yet another embodiment of the invention, there is provided a brace 10" substantially similar to brace 10 except that brace 10" is intended to be used with an existing cushioning component and an existing aligning or therapeutic component. The existing cushioning component and existing aligning or therapeutic component could be similar to the ones herein disclosed or display different characteristics without departing from the scope of the present invention. Since brace 10" is substantially similar to brace 10, the same drawings are used to illustrated brace 10 and 10", brace 10" being referred to as brace 10 throughout the drawings.

Similarly to brace 10, brace 10" includes a mounting component 22 for mounting brace 10" to a chosen body part of an intended user such as a leg or other suitable body part. Similarly to brace 10, brace 10" includes a first attachment component 26 attached to the mounting component 22 for attaching the existing alignment component 30 to the mounting component 22 so that at least a portion of the alignment component 30 is positioned substantially over the chosen body part 14 when the mounting component 22 is mounted on the chosen body part of the intended user.

Similarly to brace 10, brace 10" also includes a second attachment component 28 for attaching the existing cushioning component 32 to the mounting component 22. The second attachment component 28 is typically in a substantially superposed relationship relative to the first attachment component 26 so that the alignment component 30 is positioned between the chosen body part and the cushioning component 32 when the mounting component 22 is mounted on the chosen body part of the intended user.

Typically, the first attachment component 26 allows for releasable attachment of the alignment component 30 to the mounting component 22 and the second attachment component 28 allows for releasable attachment of the cushioning component 32 to the mounting component 22.

Similarly to brace 10, brace 10" may include a therapeutic component 34 for promoting the health of the knee. The therapeutic component 34 is typically releasably attachable to the mounting component 22 by the first attachment component 26. Brace 10" can be used either with any combination of alignment component 30, cushioning component 32 or therapeutic component 34 without departing from the scope of the present invention.

When used with both an alignment component 30 and a therapeutic component 34, the alignment component 30 and the therapeutic component 34 are adapted to be alternatively attached to the mounting component 22 by the first attachment component 26.

What is claimed is:

1. A brace usable by an intended user for aligning and protecting a patella, said patella being part of a knee of a leg of an intended user, said knee defining a femoral notch, said patella being attached to a patellar tendon, said brace comprising:
 a mounting component for mounting said brace to said leg of said user;
 a first attachment component permanently attached to said mounting component; a second attachment component permanently attached to said mounting component, said second attachment component
 an alignment component for aligning said patella, said alignment component being attached to said mounting component by said first attachment component and operative for centering said patella in said femoral notch when said brace is operatively worn by said intended user, said alignment component including an alignment pad, said alignment pad being provided with an alignment aperture, said alignment aperture defining an alignment aperture inner edge, said alignment aperture inner edge being configured and sized for substantially surrounding at least a portion of said patella of said intended user, said alignment pad being configured and sized for protecting the patella from pressure exerted by overlying structures of said brace when said brace is operatively worn by said intended user; and
 a cushioning component for cushioning said patella against impact therereon, said cushioning component being attached to said mounting component by said second attachment component;
 wherein said alignment component is releasably attached to said mounting component by said first attachment component and said cushioning component is releasably attached to said mounting component by said second attachment component;
 wherein said alignment and cushioning components are reattachable to said mounting component after having been detached therefrom;
 wherein said alignment and cushioning components are both detachable from and attachable to respectively said first and second mounting components with said brace operatively worn by said intended user;
 wherein said mounting component includes a substantially tubular sleeve configured and sized to be worn on said leg of said intended user, said tubular sleeve being provided with a sleeve window extending therethrough, said sleeve window being larger than said alignment aperture and substantially in register with said alignment component for allowing at least a portion of said alignment component to be in a more proximal relationship with the knee of the intended user then it would be without the sleeve window;
 whereby said brace allows the intended user to customize said brace depending on a level of recovery reached by the intended user by selectively attaching and detaching at least one of the alignment and cushioning components to and from the mounting component without taking off said brace.

2. A brace as recited in claim 1 further comprising a therapeutic component for promoting the health of said knee, said therapeutic component being releasably attachable to said mounting component by said first attachment component; wherein said alignment component and said therapeutic component are adapted to be alternatively attached to said mounting component by said first attachment component.

3. A brace as recited in claim 2 wherein said therapeutic component is a thermal component for changing the temperature of said knee of said intended user.

4. A brace as recited in claim 2 wherein said therapeutic component is an icing pad for icing said knee of said user, said icing pad being provided with an icing pad aperture extending therethrough, said icing pad aperture defining an icing pad aperture peripheral edge, said icing pad aperture peripheral edge being configured and sized for substantially surrounding said patella; wherein said icing pad aperture allows said icing pad to cool around said patella without directly icing said patella.

5. A brace as recited in claim 1 wherein
said first attachment component is a first attachment pocket extending from said sleeve for receiving said alignment component, said first attachment pocket being positioned so as to be substantially over said knee when said sleeve is worn by said user.

6. A brace as recited in claim 5 wherein said second attachment component is a second attachment pocket, said second attachment pocket being in a substantially overlapping relationship relative to said first attachment pocket.

7. A brace as recited in claim 6 wherein said sleeve window is substantially in register with at least a portion of said first attachment pocket for allowing said at least a portion of said first attachment pocket to be in contact with said knee of said intended user.

8. The patella brace as defined in claim 6, wherein said first and second pockets are provided outside of said sleeve.

9. A brace as recited in claim 1 wherein said alignment aperture inner edge has a substantially circular main edge segment and an auxiliary edge segment, said auxiliary edge segment being configured and sized for surrounding at least a portion of said patellar tendon.

10. A brace as recited in claim 1 wherein said alignment pad defines an alignment pad inner surface and an alignment pad outer surface, said alignment pad being provided with an abutment component extending from said alignment pad inner surface.

11. A brace as recited in claim 1 wherein said cushioning component is a cushioning pad, said cushioning pad being made of a substantially impact absorbing material.

12. A brace as recited in claim 1 wherein said alignment component allows for adjustedly medializing the position of said patella of said intended user.

13. A brace as recited in claim 12 wherein said alignment component includes a medializing tongue extending from said mounting component, said medializing tongue having a medializing aperture extending therethrough, said medializing aperture defining a medializing edge for abutting against a lateral portion of said patella.

14. A brace as recited in claim 13 wherein said alignment component is provided with an adjustment means for allowing said intended user to adjust the position of said medializing edge relative to said mounting component.

15. A brace for aligning and protecting a patella part of a knee of a leg of an intended user, said patella being attached to a patellar tendon, said knee defining a femoral notch, said brace comprising:
a mounting component for mounting said brace on said leg of said user;
an alignment component for aligning said patella, said alignment component being attachable to said mounting component through a first attachment component and operative for centering said patella in said femoral notch when said brace is operatively worn by said intended user, said alignment component including an alignment pad, said alignment pad being provided with an alignment aperture, said alignment aperture defining an alignment aperture inner edge, said alignment aperture inner edge being configured and sized for substantially surrounding at least a portion of said patella of said intended user, said alignment pad being configured and sized for protecting the patella from pressure exerted by overlying structures of said brace when said brace is operatively worn by said intended user;
a cushioning component for cushioning said patella against impacts thereon, said cushioning component being attachable to said mounting component in a substantially superposed relationship relative to said alignment component through a second attachment component;
wherein when said mounting component is mounted on said leg of said user and said alignment and cushioning components are attached to said mounting component, said alignment and cushioning components allow for simultaneous alignment and cushioning of said patella;
wherein said alignment and cushioning components are releasably attached to said mounting component;
wherein said alignment and cushioning components are reattachable to said mounting component after having been detached therefrom;
wherein said alignment and cushioning components are both detachable from and attachable to respectively said first and second attachment components with said brace operatively worn by said intended user; wherein the first and second attachment components are permanently attached to the mounting component;
wherein said mounting component is a substantially tubular sleeve configured and sized to be worn on said leg of said intended user, said tubular sleeve being provided with a sleeve window extending therethrough, said sleeve window being larger than said alignment aperture and substantially in register with said alignment component for allowing at least a portion of the alignment component to be in a more proximal relationship with the knee of the intended user then it would be without the sleeve window.

16. A brace as recited in claim 15 further comprising a therapeutic component for promoting the health of said knee, said therapeutic component being releasably attachable to said mounting component; wherein said alignment component and said therapeutic component are adapted to be alternatively attached to said mounting component.

17. A patella brace positionable adjacent a patella part of a knee of a leg of an intended user, said patella brace comprising:
a body mountable to said leg of said intended user;
first and second attachments permanently attached to said body;
a patellar guide secured to said body through said first attachment and configured and sized for aligning said patella, said patellar guide being adjacent said patella when said patella brace is operatively mounted to said leg, said patellar guide being operative for centering said patella when said patella brace is operatively worn by said intended user, said patellar guide including an alignment pad, said alignment pad being provided with an alignment aperture, said alignment aperture defining an alignment aperture inner edge, said alignment aperture inner edge being configured and sized for substantially surrounding at least a portion of said patella, said alignment pad configured and sized for protecting said patella from pressure exerted by overlying structures of said patella brace when said patella brace is operatively worn by said intended user;

a cushion for cushioning said patella against impacts thereon, said cushion being in a substantially superposed relationship relative to said patellar guide and secured to said body through said second attachment;

wherein said patellar guide and said cushion allow for simultaneous alignment and cushioning of said patella; and wherein at least one of the first and second attachments defines a pocket for removably receiving respectively said patellar guide and said cushion thereinto;

wherein said patellar guide and said cushion are both insertable into and removable from said pocket with said patella brace remaining attached to the leg;

wherein said body includes a substantially tubular sleeve configured and sized to be worn on said leg of said intended user, said tubular sleeve being provided with a sleeve window extending therethrough, said sleeve window being larger than said alignment aperture and substantially in register with said alignment component for allowing at least a portion of said patellar guide to be in a more proximal relationship with the knee of the intended user then it would be without the sleeve window.

18. The patella brace as defined in claim 17 wherein said pocket defines a pocket mouth leading thereinto and includes a releasable lock for selectively closing said pocket mouth to secure either said alignment pad therein when said alignment pad is inserted in said first pocket.

19. The patella brace as defined in claim 18, wherein said releasable lock is selected from opposed cooperating strips of miniature hook and loop fasteners extending opposed to each other across the pocket mouth, a zipper-type mechanism and a locking flap.

* * * * *